United States Patent [19]

Hornung

[11] Patent Number: 4,863,443

[45] Date of Patent: Sep. 5, 1989

[54] AUTOMATIC SPRAY APPARATUS

[75] Inventor: Richard Hornung, Dagsboro, Del.

[73] Assignee: Sterwin Laboratories Inc., Millsboro, Del.

[21] Appl. No.: 144,059

[22] Filed: Jan. 15, 1988

[51] Int. Cl.[4] .......... A61M 35/00

[52] U.S. Cl. .......... 604/289; 604/294; 604/131; 604/141; 604/144; 604/156; 128/200.14

[58] Field of Search .......... 604/93, 141, 145, 281, 604/131, 156, 152-155, 290, 294, 146-147, 310, 311, 24, 144; 128/200.14-200.27, 205.27, 205.29; 119/1, 15, 159, 160, 289

[56] References Cited

U.S. PATENT DOCUMENTS

| | | | |
|---|---|---|---|
| 2,847,993 | 8/1958 | Woodruff | 128/200.21 |
| 2,918,063 | 12/1959 | Tucker . | |
| 2,984,240 | 5/1961 | Eames | 119/160 |
| 3,051,173 | 8/1962 | Johnson et al. . | |
| 3,434,474 | 3/1969 | Reynolds | 128/200.14 |
| 3,502,079 | 3/1970 | Simmons et al. | 128/200.14 |
| 3,641,998 | 2/1972 | Lyon et al. . | |
| 3,964,481 | 6/1976 | Gourlandt et al. . | |
| 4,108,176 | 8/1978 | Walden . | |
| 4,177,810 | 12/1979 | Gourlandt . | |
| 4,276,879 | 7/1981 | Yiournas . | |
| 4,316,464 | 2/1982 | Peterson | 604/290 |
| 4,449,968 | 5/1984 | Peterson | 604/290 |
| 4,480,586 | 11/1984 | Lague et al. | 119/160 |
| 4,515,590 | 5/1985 | Daniel . | |
| 4,537,748 | 8/1985 | Billiet | 128/205.29 |
| 4,613,328 | 9/1986 | Boyd . | |
| 4,643,354 | 2/1987 | Stowe | 128/200.14 |

FOREIGN PATENT DOCUMENTS

| | | |
|---|---|---|
| 1075102 | 4/1980 | Canada . |
| 2276838 | 1/1976 | France . |
| 2276839 | 1/1976 | France . |
| 2466238 | 4/1981 | France . |
| 1242060 | 8/1971 | United Kingdom . |
| 1452790 | 10/1976 | United Kingdom . |

*Primary Examiner*—Max Hindenburg
*Assistant Examiner*—K. M. Reichle
*Attorney, Agent, or Firm*—Wendell Ray Guffey; Thomas L. Farquer

[57] ABSTRACT

Apparatus for typically delivering a measured quantity of liquid to a small animal comprising:

a spray nozzle for producing an atomized stream of liquid;

a syringe in fluid communication with the spray nozzle for delivering a measured quantity of the liquid from a liquid source to the spray nozzle;

means for actuating the syringe to deliver the measured quantity of liquid activated by a compressed air signal from a compressed air source;

means for regulating the compressed air signal to deliver to the spray nozzle a portion of the compressed air signal for atomizing the measured quantity of liquid; and means for transmitting the compressed air signal simultaneously to the actuating means and to the regulating means.

8 Claims, 3 Drawing Sheets

AUTOMATIC SPRAY APPARATUS

BACKGROUND OF THE INVENTION

1. Field of the Invention

The subject invention relates to an apparatus for automatically spraying liquid onto small animals. In particular, the invention relates to apparatus for spray treatment of small animals simultaneously with a subcutaneous injection.

2. Description of Related Art

Commercial hatcheries and other establishments administer vaccines and other liquid substances in precisely measured quantities to small animals such as chicks, ducklings, young turkeys, and guinea fowl. Devices are available for subcutaneous injection of liquids into such animals. One such device is described in U.S. Pat. No. 4,108,176. However, subcutaneous injection is not the administration method of choice in many cases.

Topical application often is the preferred method of administering certain substances to small animals. An example of such a substance is Newcastle Bronchitis vaccine for chicks, which is most effectively administered by delivery into the eyes of chicks.

Newcastle Bronchitis vaccine typically is administered by pumping a measured dose of vaccine into the mouth of a chick during the debeaking procedure or by simultaneously spraying a plurality of chicks in one spray compartment. However, neither method is entirely satisfactory. Oral administration during debeaking is unsatisfactory because chicks typically swallow most of the vaccine, thus decreasing its effectiveness. Further, hatcheries typically do not debeak chicks. Mass spraying a plurality of animals fails to ensure that each animal receives the prescribed dose. Also, the fine vaccine mist is inhaled by the chicks, causing overreaction and illness.

It is an object of this invention to provide apparatus for topically administering individual doses of desired substances to small animals.

It is a further object of this invention to provide apparatus for individually administering precisely measured topical doses of desired substances to small animals in combination with subcutaneous injection thereto.

Another object of this invention is to provide apparatus for typically administering individual doses of desired substances which is adapted for use with automatic injection apparatus known in prior art.

Yet another object of this invention is to provide apparatus for topically administering individual doses of desired substances to the eyes of small animals during subcutaneous injection thereof.

SUMMARY OF THE INVENTION

In accordance with these and other objects, this invention relates to spray apparatus for topically delivering a measured quantity of liquid to a small animal comprising:

a spray nozzle for producing an atomized stream of liquid;

a syringe in fluid communication with the spray nozzle for deliverying a measured quantity of the liquid from a liquid source to said spray nozzle;

an actuation device for actuating said syringe to deliver the measured quantity of liquid activated by a compressed air signal from a source of compressed air;

a regulation device for regulating the compressed air signal to deliver to said spray nozzle a portion of said compressed air signal for atomizing the measured quantity of liquid; and a conduit for transmitting the compressed air signal simultaneously to said actuating means and to said regulating device.

DETAILED DESCRIPTION OF THE INVENTION

The apparatus of this invention is suitably used to deliver atomized liquid to small animals. The apparatus requires that an air signal be supplied to cause the delivery of atomized liquid. Numerous ways of generating this signal are known in the art and are appropriately used to generate the required signal.

The apparatus of this invention is also suitable for use with a variety of automatic subcutaneous injection devices known in the art. In particular, the invention will be described herein in relationship to the automatic subcutaneous injection device described in U.S. Pat. No. 4,108,176, the disclosure of which is incorporation herein by reference. However, the invention is not limited to use with this particular device, but can be used either alone or with any similar pneumatically-operated device which provides a compressed air signal essentially simultaneously with the time of the injection.

Figure 1:
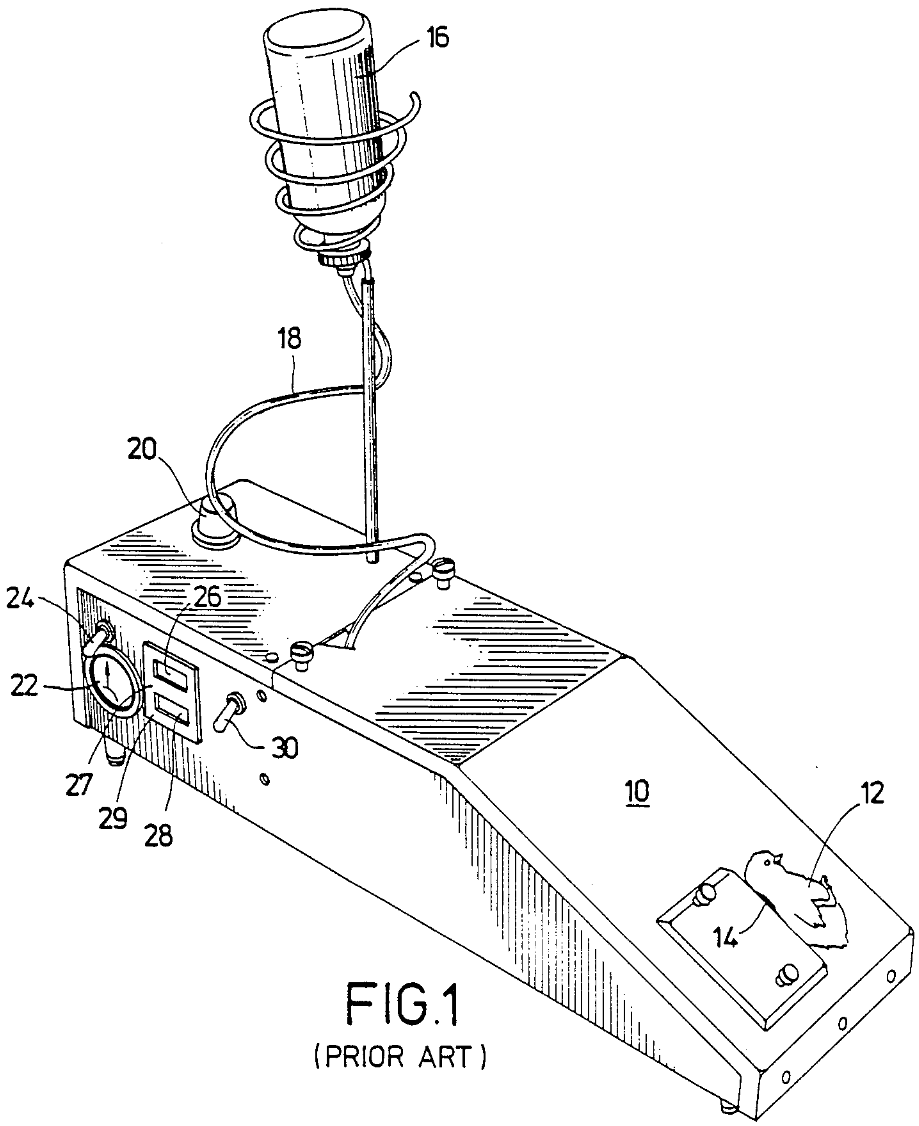
FIG.1 (PRIOR ART)
FIG. 1 is a perspective view of an injection device known in the prior art and showing a chick in position for an injection.

FIG. 1 depicts a known automatic injection device comprising features typically found on such a device, e.g., work plate 10 on which a chick 12 is shown positioned for an injection, means 14 for detecting the presence of the animal to be injected in position on work plate 10 and for actuating means (not visible in FIG. 1) for injecting the animal, a container 16 for a liquid, such as vaccine, to be injected into the animal, a tube 18 for conducting the liquid from container 16 to a syringe (not visible in FIG. 1), pressure regulator control 20, pressure gage 22, on/off switch 24, batch counter 26, batch reset button 27, cumulative counter 28, cumulator reset button 2, and test switch 30. The purpose of the test switch is to allow the operator to ensure that the injection device protrudes sufficiently from work plate 10 so that the animal is properly injected. The functions of the remainder of the devices are self-evident. The above-identified devices are typically present on pneumatically-operated automatic injection devices, but each need not be present on any automatic injection device to which the spray apparatus of this injection may be connected. As noted above, the only necessary feature is that the injection device provide a compressed air signal essentially simultaneously with the time of the injection.

Figure 2:
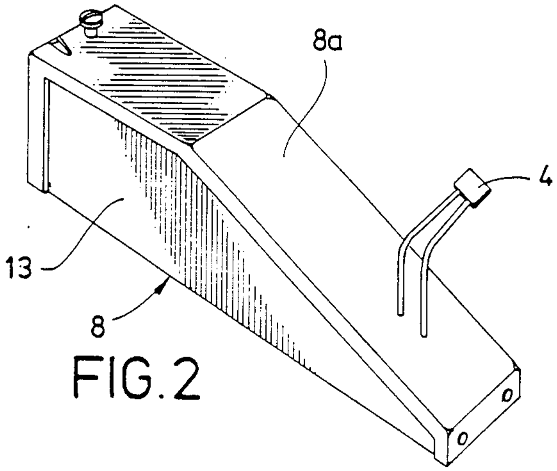
FIG. 2 shows a view of the invention before it is attached to an injector.

FIG. 2 depicts apparatus 13 for delivering a measuring portion of liquid in the form of an atomized spray essentially simultaneously with the injection. The outside covering 8 of the apparatus typically is shaped to confrom with the covering of the injection apparatus, as is illustrated in the figure. However, any shape is satisfactory which positions spray nozzle 4 so that the atomized spray is delivered to the desired part of animal 12. For example, Newcastle Bronchitis vaccine preferably is delivered to the eyes, so the nozzle is suitably adjusted for this application. Cover 8a conveniently is hinged to provide access to the interior of the apparatus. The outside covering of the apparatus may be made of any durable material which is easily cleaned, such as stainless steel.

Figure 3:
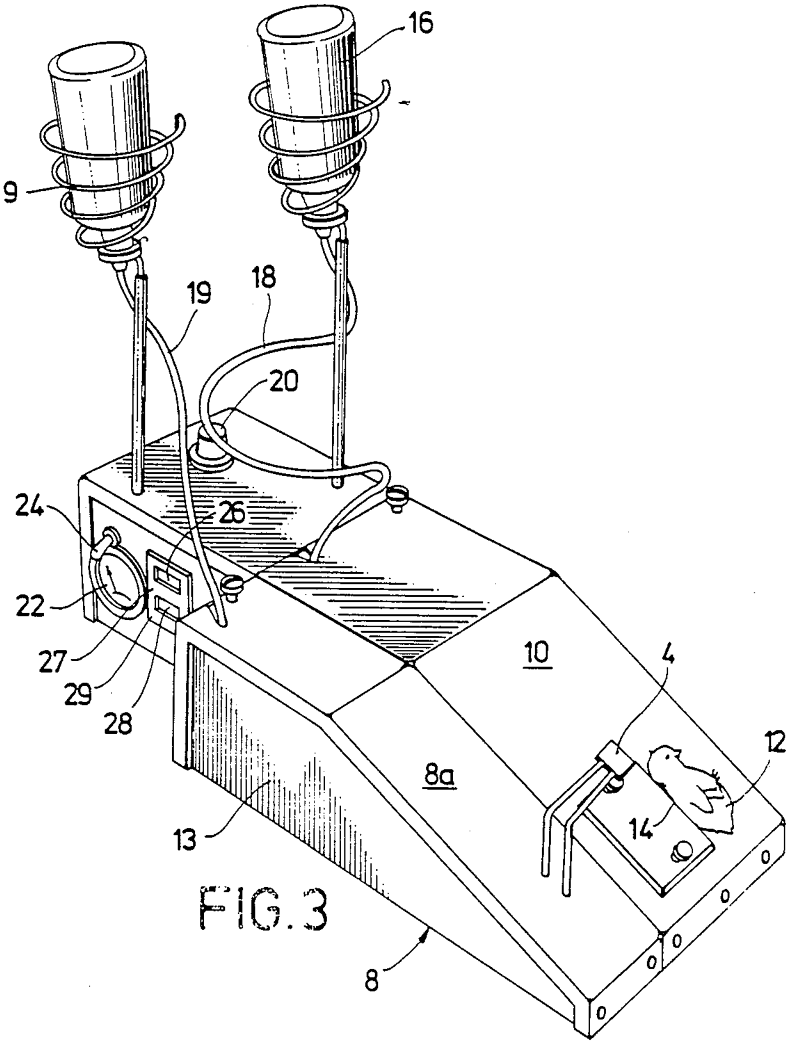
FIG. 3 shows the apparatus of the invention after it has been attached to an injector.

FIG. 3 illustrates the relationship between the apparatus of the invention 13 and a known automatic injection device. The figure illustrates spray nozzle 4 in position to deliver an atomatized liquid to the eyes of animal 12, in position on the automatic injection device. Container 9 is the source of the liquid which is conveyed to a syringe in apparatus 13 (not shown) through tube 19. Apparatus 13 can be permanently or removably attached to the injection device in any suitable manner which positions spray nozzle 4 to delivery atomized liquid to the desired part of the animal.

Figure 4:
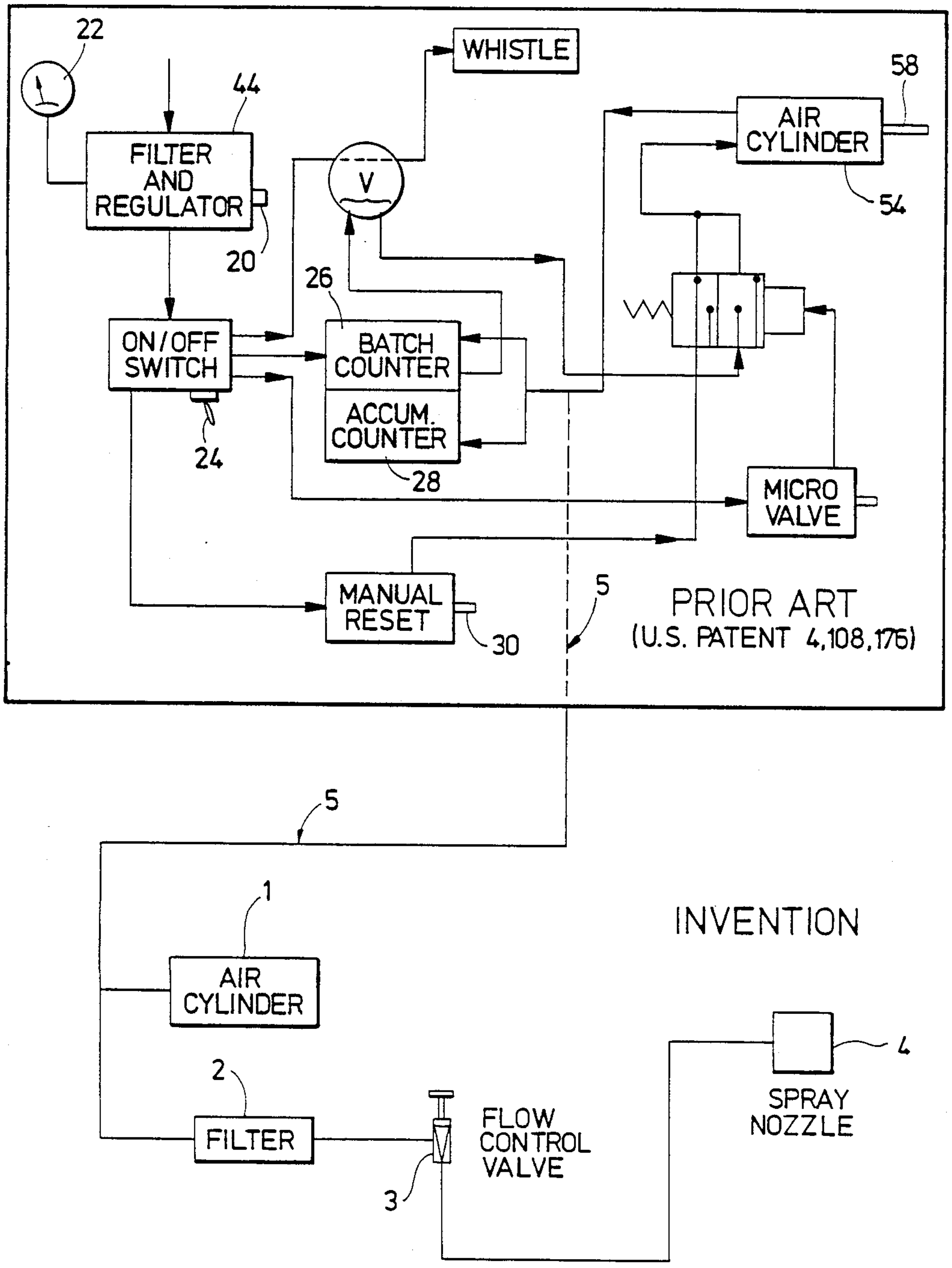
FIG. 4 is a schematic diagram of the pneumatic circuitry of the invention, including the relationship of the circuitry to that of a known subcutaneous injection device.

FIG. 4 illustrates the pneuamtic circuitry of the apparatus of the invention and its relationship to the circuitry of the device described in U.S. Pat. No. 4,108,176. As noted above, the apparatus of the invention can be utilized with any injection device which provides a compressed air signal essentially simultaneously with the time of injection. Such a signal is produced whenever cylinder 54 of the injection device operates a syringe (not shown) to inject an animal. This compressed air signal is transmitted from the injection device to apparatus 13 through conduit 5.

Conduit 5 transmits the signal simultaneously to air cylinder 1 and flow regulation device 3 in apparatus 13. Actuation of air cylinder 1 causes the syringe of the apparatus (not shown) to deliver a measured quantity of liquid to spray nozzle 4. Simultaneously, the signal is transmitted to flow regulation valve 3, which delivers to spray nozzle 4 a portion of the compressed air signal for atomizing the measured quantity of liquid. The remainder of this air signal is exhausted. Devices such as the flow regulation valve and the air cylinder are well-known to those skilled in the art, so further description of the details of their operation is unnecessary. Those skilled in the art will be able, for example, to adjust the quantity of air supplied to the spray nozzle to achieve delivery of a desired amount of atomized liquid to the animal.

The precise mixture of liquid and air delivered to spray nozzle 4 produces finely atomized liquid which is topically delivered simultaneously with the injection of the animal. The flow of air provided to spray nozzle 4 is regulated by flow regulation valve 3 to provide an amount to atomize the desired amount of liquid and to provide sufficient velocity to the atomized liquid to propel it onto the animal. The required liquid velocity depends upon the distance of spray nozzle 4 from the animal being treated and the density and size of the liquid droplets. Operators of the apparatus will easily be able to adjust the compressed air flow to achieve these purposes.

Figure 5:
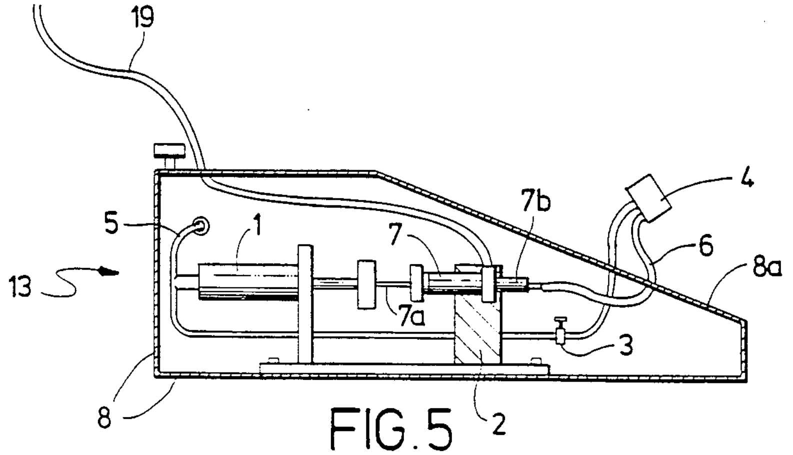
FIG. 5 is a side view with the cover broken away to expose the interior to the device.

Turning now to FIG. 5, one can see the entirety of the interior of apparatus 13. A compressed air signal is transmitted in conduit 5 from the injection device (not shown) to air cylinder 1 and flow regulation valve 3. As described above, the portion of the air signal delivered to spray nozzle 4 through the flow regulation valve 3 is that amount appropriate to atomize the liquid provided and propel the liquid droplets to the animal being treated. The remainder of the air signal is exhausted to the atmosphere.

Air cylinder 1 causes syringe 7, which comprises plunger 7*a* and barrel or cylinder 7*b*, to deliver liquid to the spray nozzle. Actuation of air cylinder 1 causes plunger 7*a* to move axially in barrel or cylinder 7*b* and deliver a predetermined quantity of liquid from liquid delivery tube 19 through liquid conduit 6 to spray nozzle 4. The liquid arrives at spray nozzle 4 simultaneously with the arrival of compressed air and is atomized for topical application to the animal being injected (not shown). Cylinder 7*b* is fixed in retaining plate 2, which is attached to outer covering 8 of apparatus 13. Any suitable method of restraining the syringe within the apparatus is appropriate for use in this invention. Conveniently, syringe 7 is removably mounted in an open slot (not shown) in retaining plate 2, which is made of a resilient material such as a resilient plastic and is attached to outside covering 8. Thus, syringe 7 can be easily snapped into place in retaining plate 2 and held in place by the resiliency of the plate. Thus, the syringe can easily be removed for inspection, repair, and cleaning.

Air cylinder 1 returns to its rest position under the influence of an internal spray or by any suitable method. Plunger 7*a* is returned to its rest position from the delivery position within cylinder 7*b* in cooperation with the restoration of the air cylinder. During this restoration, syringe 7 withdraws fluid from liquid container 9 (not shown) through liquid delivery conduit 19 into barrel 7*b* in preparation for subsequent administration.

Adjustment of the quantity of liquid delivery is also made by techniques known in the art. For example, travel (i.e., extent of axial movement of plunger 7*a*) could be limited by adjustable mechanical stops. Alternatively, retaining plate 2 could be slidably attached to the outer covering 8 of apparatus 13. For example, movement of barrel 7*b* towards air cylinder 1 would shorten the travel of plunger 7*a*, thus reducing the quantity of liquid delivered. The inside diameter of cylinder 7*b* could be reduced (the outside diameter of plunger 7*a* would also be reduced). These techniques are merely suggestions; other quantitative adjustment techniques known in the art can be utilized.

The pressure and purity of the compressed air signal will be directly related to the pressure and purity of the air supplied to the injection device by filter regulator 44 in that device, illustrated in FIG. 4. Typically, the pressure of the air supplied by the regulator to the pneumatic circuitry of the injection device is between about 30 and 60 psi. The purity depends upon the quality of that filtering device. Typically in such injection devices, the filter is designed to exclude particles of dust, dirt, and oil from the system which are larger than 40 microns. Further, additional contaminants may be introduced into the compressed air during operation of the injection device. Therefore, sub-micron filter 2 (i.e., a filter which fails to capture particles of less than 1 micron average size) is interposed to filter the compressed air signal before the signal is introduced to flow regulating device 3. Although this filter may be placed anywhere in conduit 5, preferably it is placed immediately upstream from flow regulation device 3, as illustrated in FIG. 4, to minimize the quantity of air which must be filtered. The purpose of this filter is to remove bacteria from the atomizing air flow. Therefore, the filter preferably is a 0.2 micron bacterial filter.

Atomizing spray nozzle 4 can be of any design which produces the desired atomizing spray and delivers it to the animal to be treated. At noted above, typical treatment volumes range up to about 1 mL. Desirably, the nozzle accommodates liquid flow volumes within this range.

The liquid flow volume per treatment depends upon the vaccine being delivered and the concentration thereof. Therefore, typical treatment volume range is up to about 1 mL, and can be larger. Often, the volume of a single treatment is less than about 0.1 mL. For example, the volume of Newcastle Bronchitis vaccine typically utilized is 0.03 mL. Those skilled in the art will be able to select individual components, such as the syringe, suitable for use with their application.

The following example is intended to illustrate further the invention, not to limit its scope in any way. The scope of the invention is limited only by the appended claims.

EXAMPLE 1

An automatic spray apparatus built in accordance with the invention was utilized to deliver 0.03 mL of Newcastle Bronchitis vaccine (Type $B_1$, Mass.) to the eyes of 50 one day old single combed white leghorn chicks. The vaccine contained $10^{6.02}$ $EID_{50}$ of Newcastle Bronchitis virus and $10^{4.30}$ $EID_{50}$ of infectious bronchitis virus in a standard glycerinated water solution ($EID_{50}$ equals embryo infections dose sufficient to infect 50% of the treated population). All vaccinated chicks and 20 unvaccinated controls were housed in separate Horsfal isolation cages.

The apparatus used to atomize the vaccine and deliver it to the chicks' eye was operated in conjunction with automatic subcutaneous injection device described in U.S. Pat. No. 4,108,176. Conduit 5, which transmitted the compressed air signal from the injection device to air cylinder 1 and flow regulation device 3 through a Gelman Model 4260 0.2 micron filter, was vinyl tubing having ⅛-inch inside diameter and ¼-inch outside diameter, such as A.D.I. 1331. The vaccine was supplied from a 30 mL container 9 through a ⅛-inch inside diameter by ¼-inch outside diameter vinyl tube 19 to syringe 7.

Syringe 7 (Atlas Electronics Model A-ABC-0.03) delivered a 0.03 mL liquid vaccine dose to spray nozzle 4 through A.D.I. 1331 vinyl tubing. The syringe was retained in an open slot in resilient block 2. Air cylinder 1, which operated syringe 7 upon receipt of the compressed air signal delivered through conduit 5, was a Bimba Model D-29472A. The compressed air signal was also delivered through the air filter to flow regulation device 3 (SMC Model AS 1100 -- suitable for use with air pressures up to about 60 psi.) The flow was regulated and delivered through a ⅛ inch inside diameter vinyl tube suitable for such pressure, such as A.D.I. 1331, to spray nozzle 4. Spray nozzle 4 was manufactured by Spraying Systems, Inc. and comprised a 1250 fluid cap, a 67147 air cap, and a 6552-⅛ JAC body. The distance between spray nozzle 4 and the chick being treated was adjusted to 2 inches for correct delivery of the vaccine to the chick's eyes.

Each of the 50 vaccinated chicks developed respiratory noise at about four days post-vaccination. The noise continued through about the tenth or twelfth day post-vaccination. No reaction appeared to be excessive.

Twenty-six days after vaccination, twenty-five of the vaccinated chicks and ten controls were challenged with Newcastle disease virus. These birds were observed daily for twelve days for signs of Newcastle disease. Twenty-three of the twenty-five vaccinated birds were protected, while all of the control animals died.

The remaining twenty-five vaccinated chicks and ten controls were challenged with an infectious bronchitis virus (Type Mass.). Tracheal swabs were taken at five days post-challenge, and swab samples were inoculated into ten day old embryonated eggs for virus recovery testing. No virus was recovered from the vaccine-protected chicks, but virus was recovered in each control test.

This example illustrates the effectiveness of the atomized liquid delivery apparatus to delivery an immunizing dose of liquid to chick's eyes.

Although preferred embodiment of this invention have been discussed herein, those skilled in the art with appreciate that changes or modifications may be made without departing from the spirit of the invention, as defined in and limited only by the scope of the appended claims.

I claim:

1. A spray apparatus for topically delivering a measured quantity of liquid to a small animal being simultaneously subcutaneously injected on an automatic injection apparatus which provides a compressed air signal essentially simultaneously with the injection, said spray apparatus comprising:

a spray nozzle means for producing an atomized stream of liquid for topical delivery to the small animal;

a syringe in fluid communication with the spray nozzle means for delivering a measured quantity of the liquid from a liquid source to said spray nozzle means, said syringe adapted for connection to the liquid source;

means for actuating said syringe to deliver the measured quantity of liquid in response to receipt of said compressed air signal from the automatic injection apparatus;

means for regulating the compressed air signal so as to deliver to said spray nozzle means a portion of said compressed air signal for atomizing the measured quantity of liquid; and means for transmitting the compressed air signal from pneumatic circuitry in the automatic injection apparatus simultaneously to said actuating means and to said regulating means.

2. The apparatus of claim 1, further comprising means for filtering the compressed air signal before the signal is transmitted for said regulating means.

3. The apparatus of claim 2 wherein said filtering means comprises a sub-micron filter interposed in said transmitting means.

4. The apparatus of claim 3, wherein said sub-micron filter comprises a 0.2 micron bacteria filter.

5. The apparatus of claim 1, further comprising an outside covering means for encasing said nozzle means, said syringe, said actuating means and said regulating means and a retaining plate means attached to the outside covering means for removably mounting said syringe.

6. The apparatus of claim 1, further comprising means for filtering the compressed air signal before the signal is transmitted to said regulating means.

7. The apparatus of claim 5, wherein said filtering means comprises a sub-micron filter interposed in said transmitting means.

8. The apparatus of claim 7, wherein said sub-micron filter comprises a 0.2 micron bacterial filter.

* * * * *

UNITED STATES PATENT AND TRADEMARK OFFICE

CERTIFICATE OF CORRECTION

PATENT NO. : 4,863,443

DATED : September 5, 1989

INVENTOR(S) : Richard Hornung

It is certified that error appears in the above-identified patent and that said Letters Patent is hereby corrected as shown below:

Column 1, line 34, "Following the word "spraying" insert --of--

Column 1, line 62, "deliverying" should read --delivering--

Column 2, line 36, "incorporation" should read --incorporated--

Column 2, line 54, "2" should read --29--

Column 2, line 58, "self-evidient" should read --self-evident--

Column 2, lines 67&68, "measuring" should read --measured--

Column 3, line 17, "atomatized" should read --atomized--

Column 3, line 23, "delivery" should read --deliver--

Column 3, line 25, "pneuamtic" should read --pneumatic--

Column 4, line 29, "spray" should read --spring--

Column 4, line 36, "delivery" should read --delivered--

Column 5, line 6, "at" should read --as--

Column 5, line 36, "eye" should read --eyes--

Column 6, line 15, "embodiment" should read --embodiments--

Column 6, line 16, "with" should read --will--

UNITED STATES PATENT AND TRADEMARK OFFICE

CERTIFICATE OF CORRECTION

PATENT NO. : 4,863,443

DATED : September 5, 1989

INVENTOR(S) : Richard Hornung

It is certified that error appears in the above-identified patent and that said Letters Patent is hereby corrected as shown below:

Column 6, line 49, Claim 2, "for" should read --to--

Signed and Sealed this

Sixteenth Day of October, 1990

*Attest:*

HARRY F. MANBECK, JR.

*Attesting Officer*

*Commissioner of Patents and Trademarks*